United States Patent [19]
Engelbrecht

[11] 3,994,687
[45] Nov. 30, 1976

[54] PERISTALTIC DILUTOR SYSTEM AND METHOD

[76] Inventor: Eduard Engelbrecht, Park Vronesteyn 49, Voorburg, Netherlands

[22] Filed: Oct. 10, 1974

[21] Appl. No.: 513,734

Related U.S. Application Data

[63] Continuation-in-part of Ser. No. 308,783, Nov. 22, 1972, abandoned.

[30] Foreign Application Priority Data

| Nov. 24, 1971 | Switzerland | 17132/71 |
| Jun. 22, 1972 | Switzerland | 9402/72 |
| Nov. 21, 1972 | France | 72.42147 |
| Nov. 22, 1972 | United Kingdom | 54165/72 |

[52] U.S. Cl. ............................. 23/230 R; 23/259
[51] Int. Cl.² ................. G01N 1/00; G01N 31/00
[58] Field of Search ............... 23/259, 253, 230 R, 23/230 A, 253 A; 417/12, 477; 222/63, 76, 207; 318/265; 261/121 R

[56] References Cited
UNITED STATES PATENTS

| 3,241,921 | 3/1966 | Ferrari | 23/253 R |
| 3,437,895 | 4/1969 | Peters | 318/265 X |
| 3,475,128 | 10/1969 | Thiers | 23/230 R |
| 3,666,420 | 5/1972 | Paatzsch | 23/253 R |
| 3,737,251 | 6/1973 | Berman et al. | 417/12 |

*Primary Examiner*—Robert M. Reese
*Attorney, Agent, or Firm*—Kurt Kelman

[57] ABSTRACT

Geometric dilution of a liquid is effected in a series of successive containers through a flexible tube having an upstream end in communication with a diluent liquid supply and a downstream end in successive communication with each of the successive containers. A peristaltic pump is arranged between the upstream and downstream tube ends and the pump has a rotor with rollers distributed concentrically about the rotary shaft of the rotor and angularly spaced equidistantly thereabout. The flexible tube is laced between the pump rollers and a concavely arcuate pumping shoe to occlude the tube locally at equidistantly spaced points along the length of the tube during rotation of the rotor. The rotor is gently entrained through predetermined angular portions of a full rotation in alternate directions in such a way that the rollers are always located in the same angular position when the rotor is arrested. Rotation in one direction pumps a first dose of the liquid at the downstream tube end inwardly and rotation in the opposite direction for a second and larger angular portion pumps outwardly the first dose of liquid and a dose of the diluent liquid pumped from the upstream tube end.

3 Claims, 9 Drawing Figures

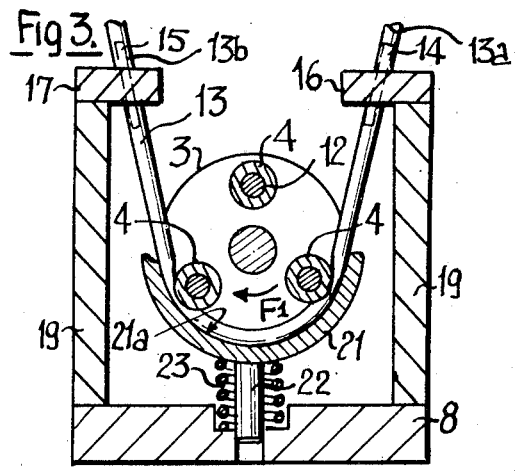
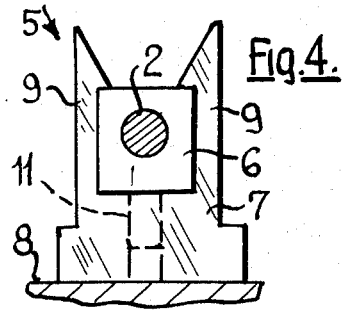
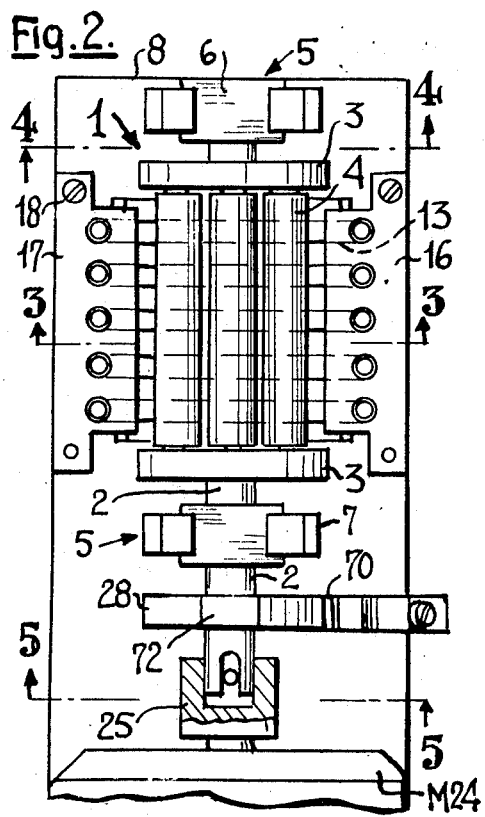
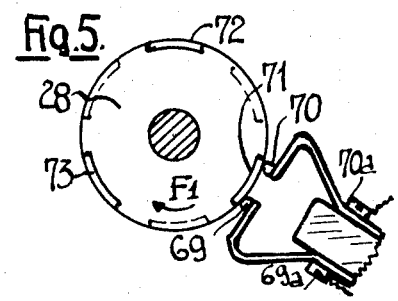
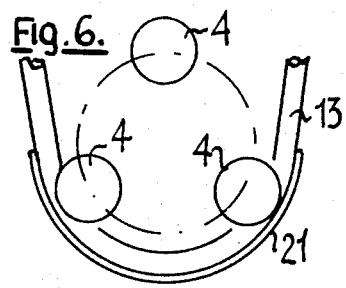
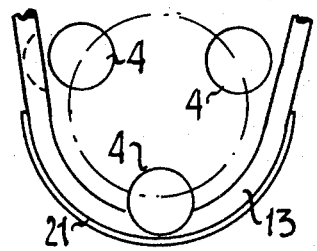

PERISTALTIC DILUTOR SYSTEM AND METHOD

The present application is a continuation in part of my copending application Ser. No. 308,783, filed Nov. 22, 1972, now abandoned. The present invention relates to improvements in a peristaltic dilutor system for the preparation of liquid dilutions in research and analytic laboratories, and to a method of geometrically diluting liquids.

In operations of this type, precise quantities of liquids must be distributed into test tubes, and it has been proposed, for example, to do this with a syringe. Where repeated dosing of liquid diluents are required, peristaltic pumps have been used for this purpose, such peristaltic dilutor systems comprising one or more flexible tubes whereon a power-driven rotor acts to propel liquid through the tube or tubes.

Known systems of the latter type comprise a flexible tube having an upstream end and a downstream end, a supply of diluent liquid in communication with the upstream end of the flexible tube for filling the tube with diluent liquid, and a peristaltic pump arranged between the upstream and downstream tube ends. A concavely arcuate pumping shoe is mounted for cooperation with rollers mounted on a rotor of the pump, the tube being compressed by the rollers pressing it against the shoe when the rotor rotates the rollers into engagement with the tube whereby the tube is locally occluded at successive points and the liquid filling the tube is peristaltically propelled therethrough. Dosing of the propelled liquid is obtained by a timing device which causes intermittent stoppage of the rotor rotation to enable the container of the propelled liquid to be replaced.

It has been difficult to obtain equal and regular doses of liquid with this known type of peristaltic dilutor system because the timed rotor stoppage may cause the rotor to be stopped in successive angular positions in which the state of compression of the flexible tube or tubes is not the same, which leads to considerable variations in the liquid doses. In fact, if stopping occurs when the pressure roller disengages from the tube, the resultant inflation of the flexible tube at this point causes a reverse stream of liquid which disturbs the uniformity of the dosage distributed by the apparatus.

Inaccurate metering will also result from a disparity in the number of rollers compressing the tubes during successive meterings, as well as from differences in the degree of stretching of the tubes resulting from variations in the angular position of the rollers at the successive arrests.

It is a primary object of this invention to overcome these disadvantages and to provide a peristaltic pump in a dilutor system of the described type which permits the repeated distribution of very precise doses of liquid.

It is another object of the invention to provide an improved method for geometrically diluting a liquid in a series of successive containers with a diluent liquid.

This is accomplished in accordance with the present invention with control means for intermittently entraining the peristaltic pump rotor for rotation through predetermined angular portions of a full rotation in alternate directions stopping every time in an identical predetermined angular position. Rotation in one direction for a first angular portion propels a first predetermined dose of the liquid at the downstream end of the flexible tube inwardly, and rotation in the opposite direction for a second and larger angular portion propels outwardly at the downstream tube end the first dose of liquid and a predetermined dose of the diluent liquid propelled by the pump from the upstream end of the tube. Accurate metering is assured by providing rollers distributed concentrically about the rotary shaft of the rotor and angularly spaced equidistantly thereabout whereby the propelled liquid is divided into equal doses by two of the rollers being in occluding contact with the flexible tube the rollers always being located in an identical angular configuration when in the stopping position.

The method of this invention comprises the combination of steps of peristaltically pumping accurately metered doses of the diluent liquid through a flexible tube from an upstream end of the tube in communication with a supply of the diluent liquid to a downstream end of the tube in successive communication with each of the successive containers, the downstream tube end holding a selected number of the metered doses of the diluent liquid, immersing the downstream tube end in a first one of the successive containers containing the liquid to be diluted, peristaltically pumping an accurately metered dose of the liquid from the first container, withdrawing the downstream tube end holding the accurately metered dose of the liquid to be diluted and the diluent liquid from the first container, immersing the downstream tube end in a second one of the successive containers, peristaltically pumping the metered dose of the liquid to be diluted and the selected number of metered doses of the diluent liquid into the second container, mixing the liquid to be diluted and the diluent liquid in the second container to obtain an accurately metered dose of a first diluted liquid, and continuing the cycle of withdrawing and immersing the downstream tube end, peristaltic pumping and mixing in successive ones of the containers.

The above and other objects, advantages and features of the invention will become more apparent from the following detailed description of a now preferred emodiment thereof, taken in conjunction with the accompanying drawing wherein FIG. 1 is a side elevational view of the apparatus of this invention;

FIG. 2 is a plan view, on an enlarged scale, of the peristaltic pump in the apparatus;

FIGS. 3, 4 and 5 are respective sections along lines 3—3, 4—4 and 5—5 of FIG. 2;

FIGS. 6 and 7 are schematic views illustrating different types of operation of the peristaltic pump;

Figure 1:
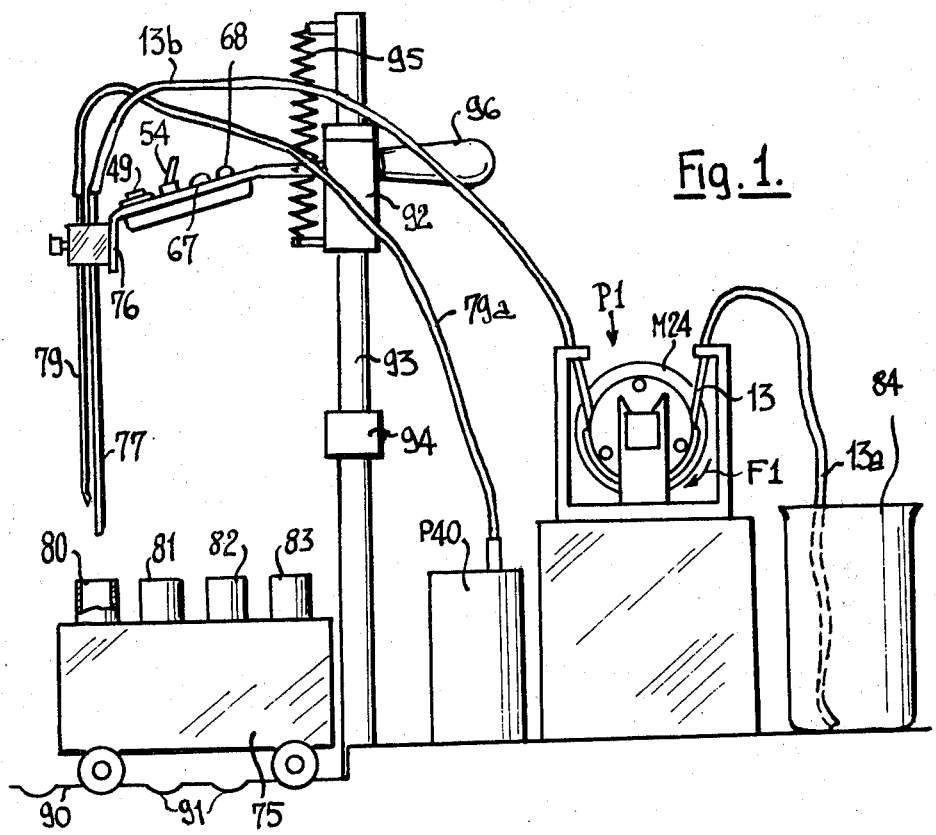

The apparatus for the preparation of dilutions comprises peristaltic pump P1 shown in detail in FIGS. 2 to 5. This pump comprises a plurality of parallel flexible tubes 13 (see FIG. 2). As shown in FIG. 1, the downstream portion 13b of each tube is connected to a small tube or nozzle 77 which is mounted on a vertically movable support 76. The upstream portion 13a of each tube 13 is immersed in, and opens into, reservoir 84 containing a supply of dilution liquid.

The nozzles 77 associated with each of the tubes 13 of the peristaltic pump are disposed on the same support 76 for common vertical movement and are periodically immersed into respective tubes or containers 80, 81, 82, 83 which are arranged parallel to each other in series of successive containers, the containers being mounted in a common support carriage 75. FIG. 1 shows only one of the nozzles 77 and the corresponding containers 80 to 83, the other nozzles and their corresponding containers not being visible in the side view of FIG. 1 since they are aligned with the illustrated nozzle and containers. As shown in FIG. 1, a nozzle 79 is associated in parallel position with each nozzle 77 and has its upper end connected to electrical air pump P40 while its lower end is biased towards, but is located above, the outlet of associated nozzle 77. When air is fed to nozzle 79, an oblique air stream is blown on the surface of any liquid delivered through nozzle 77 without being mixed therewith.

The support carriage 75 runs on track 90 represented by notches 91 marking the positions wherein the carriage is manually displaced to bring the series of successive containers 80 to 83 successively under, and into alignment with, nnozzle 77.

The support 76 is affixed to slide 92 glidably carried on column 93. In this manner, the support may be moved between an upper position (shown in FIG. 1), wherein the nozzles 77 are outside the containers, and a lower position, defined by stop 94 on column 93, wherein the ends of the nozzles are positioned close to the bottom of the containers. A compression spring 95, having one end attached to slide 92 and the other end to the column 93, biases the assembly upwardly, a handle 96 being provided for moving it along the column.

It is, of course, possible to reciprocate the nozzles and/or to move the carriage 75 by electrical or mechanical means other than those illustrated and described herein merely by way of example.

Referring now more particularly to FIGS. 2 to 4, the pump P1 comprises a rotor 1 mounted on shaft 2 which carries two annular discs 3, 3 wherebetween there are arranged three pressure rollers 4 freely rotatably mounted on the discs by means of rods 12 and spaced equidistantly in a concentric circle about shaft 2 of the rotor, i.e. the pressure rollers are spaced apart by 120°. The shaft is journaled for rotation in two bearings 5 each constituted, as shown in FIG. 4, by bearing block 6 in whose bore the shaft rotates. The bearing blocks are supported in a bracket 7 which is affixed to a base support 8. The bracket, which may be of plastic material has two prongs 9, 9 forming a seat for the bearing block. Due to their resiliency, the prongs of the bracket may be deformed and moved apart to enable the bearing block to be removed, the bearing block having a guide pin 11 extending into a mating recess or hole in bracket 7.

As explained hereinabove, the bearing blocks 6 of rotor shaft 2 may be readily removed from brackets 7 to remove the rotor. Thus, the tubes 13 may also be disengaged and removed from the pump after the mounting plates 16 and 17 have been unscrewed. This arrangement makes the replacement of the tubes easy and also facilitates their sterilization.

Each flexible tube 13, which will suitably be made of a flexible plastic material inert to the liquids handled, is substantially U-shaped in the region of the pump and, as shown in FIG. 2, the tubes are disposed in parallel relationship and are held in place by tubular connectors 14, 15 arranged on plates 16, 17 which are detachably mounted by screws 18 on lateral walls 19 extending upwardly from base support 8 of the pump, the rotor of the pump being arranged intermediate the connectors 14, 15 so that the flexible tubes may be laced about the rotor to form the U-shaped tube portions shown in FIG. 3.

The flexible tubes 13 are always compressed simultaneously by a pair of rollers 4, when at rest. Which press them against the semi-cylindrical pumping shoe 21, the tubes being laced between the rollers and the shoe. The shoe is supported by rods 22 gliding in mating bores in base support 8, compression springs 23 being interposed between the casing and the base support to bias the shoe upwardly against a pair of pressure rollers 4 into engagement with the flexible tubes.

When the rotor is rotated, the rollers 4 will successively press engaged sections of the tubes 13 against the concave arcuate support surface of shoe 21, occluding the tubes at points progressing along the tubes and thus propelling liquid contained in the tubes therealong in a peristaltic manner.

Figure 8:
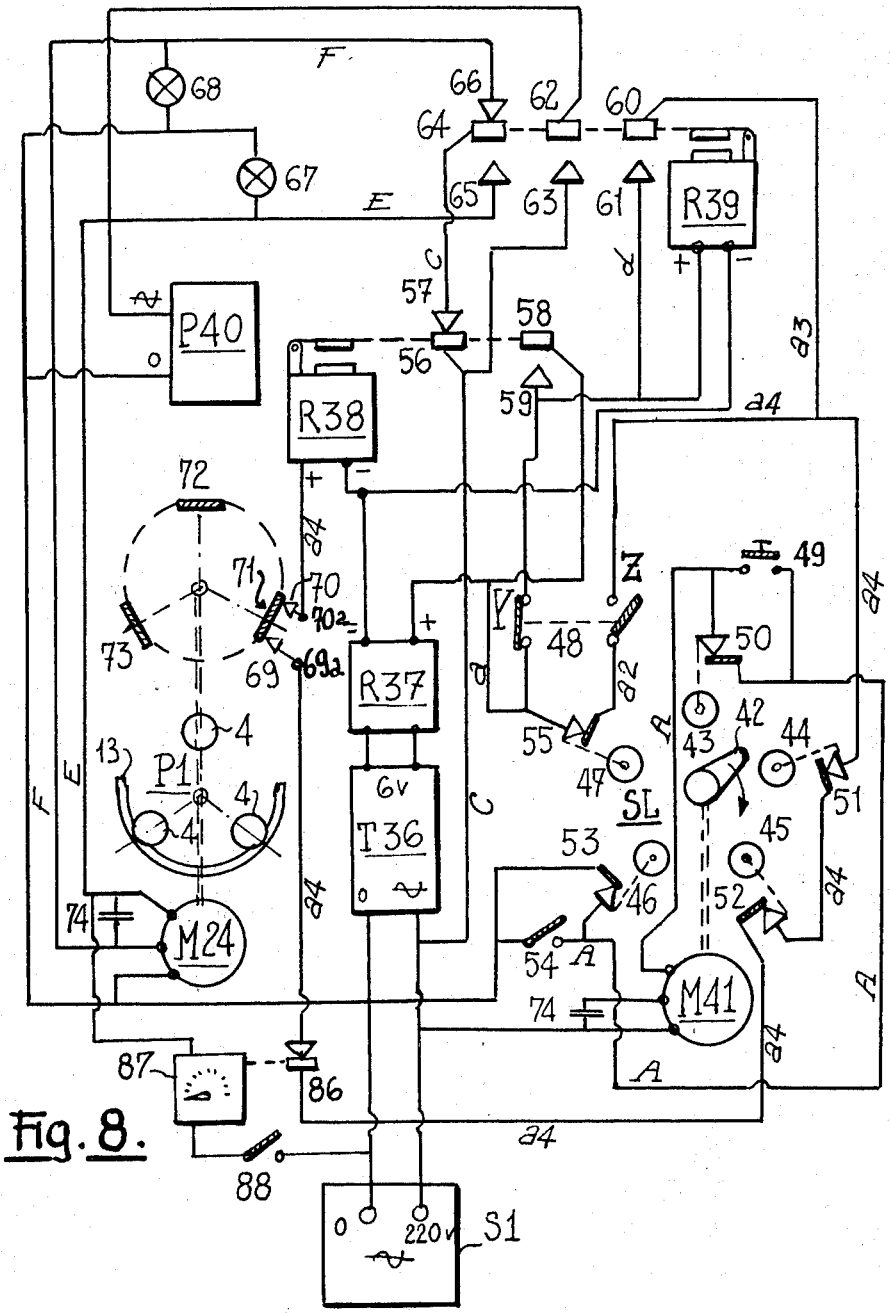
FIG. 8 is a diagram of the electric control circuit for the operation of the pump.

Rotor 1 is connected by means of a detachable coupling 25 to a conventional motor M24 which is under the control of the circuit illustrated in FIG. 8 to entrain the rotor intermittently in a predetermined cycle and in alternating directions over predetermined angular sections of a circle. Furthermore, the control circuit always immobilizes the rotor in the angular position illustrated in FIG. 6, wherein the tubes 13 are compressed by two rollers 4.

The control for the rotor 1 of the pump comprises an insulating collar 28 mounted on rotary shaft 2 and carrying three contact blades 71, 72, 73 spaced apart 120° (see FIGS. 2 and 5). In the illustrated stop position, blade 71 makes contact between contact elements 69 and 70 connected to terminals 69a and 70a of an electric circuit a4 which connects an interrupter Z of a double interrupter switch 48 and a relay R38 (see FIG. 8).

Closing of the switch contact Z permits relay R38 to receive current from current source S1, a transformer T36 and a rectifier R37 being connected between the current source and the relay. The current feed line includes switch 55 (closed for this purpose), circuit line a2 between switch 55 and switch Z, also closed, circuit line a4 including switches 51, 52 and 86, all closed, and the contact blade 71.

Operation of relay R38 has the effect of opening switch 566, 57 in feed circuit line C leading to motor M24 of pump P1 so that the power to the motor is cut and the rotor is at rest. The motor feed line C also includes a second, current inverting switch 64/65/66 operated by relay R39. The latter switch permits the circuit line C to be connected selectively to two different circuit lines serving to supply power to motor M24, i.e. lines E or F.

The actuation of relay R38, subsequent to the closure of switch Z of the double switch 48, also causes actuation of relay R39 by closure of switch 58/59 which is operated by relay R38, the two relays being electrically connected.

Operation of relay R39, closes switch 60/61 so that the relay R39 will receive current independently of the state of switch 58/59 by circuit line a3 connected to switch 60/61 and circuit line d.

Actuation of relay R39 also closes switch 64/65 in circuit line C so that the latter becomes connected to the circuit line E leading to motor M24. Thus, the motor receives power and rotates rotor 1 in clockwise direction when the switch 56/57 operated by relay R38 is closed by means of a selector device to be described hereinafter.

The operation of relay R39 also closes switch 62/63 to operate the motor of an air pump P40. This pump, as shown in FIG. 1, feeds air through tubes 79a and biased nozzles 79 which are coupled to the nozzles 77 and eccentrically located in the receptacles so that the dilutions in receptacles 80 to 83 will be stirred by the rotary movement of the fluid, induced by the air stream biased against the surface, when the nozzles 77 supply liquid thereto.

The selector device SL in the pump motor control circuit comprises five switches 50, 51, 52, 53, and 55 controlled by respective cam follower rollers 43, 44, 45, 46 and 47 engaging the camming surface of a rotary cam 42 entrained by motor M41. Power is supplied to this motor by circuit line A which includes switch 50 operated by roller 43 and a manually operable switch 49 in parallel with switch 50. Initially, the cam 42 keeps switch 50 open and the motor M41, therefore, receives no power.

To operate the selector SL, the switch button 49 is briefly depressed to actuate motor M41 through circuit line A which includes switch 53 of the selector which, therefore, is also closed. As soon as the motor M41 is operated, switch 50 is closed and the cam 42 turns. It first actuates switch 51 operated by cam follower 44, thus briefly interrupting current supply to relay R38 through circuit line a4. During this brief moment of interruption and since switch 56/57 is closed, motor M24 of the pump rotor is started since the circuit line C is connected to circuit line E of motor M24. At the same time, a lamp 67 lights up to signal the motor operation visibly. The rotor turns clockwise when fed by supply line E, as indicated by arrow F1 in FIGS. 1 and 3, causing liquid to be passed through the tubes 13 from their upstream portion 13a to their downstream portion 13b.

Rotation of rotor 1 causes the blade 71 to move away from contact elements 69, 70 so as to interrupt circuit a4 which accordingly remains open until next blade 72 closes contact 69, 70 again when the rotor has made a one third turn in the clockwise direction (see FIG. 5). The resultant operation of relay R38 stops the rotor in this new angular position, due to the reopening of switch 56/57.

On further rotation and shortly thereafter, the cam operates switch 52 controlled by cam follower 45 and the above-described cycle is repeated so that the rotor again turns one third of one full rotation in a clockwise direction until the blade 73 connects the contact elements 69 and 70. In this way, the rotor turns clockwise in two 120° steps and lamp 67 signals these two movements.

It will be noted that the switch 86 in circuit line a4, which is normally closed, may be under the control of an adjustable timing device 87 will keep the switch open for a controlled time interval, counting from the beginning of the power feed to motor M24. To place the device 87 in service, switch 88 is closed. As long as the switch 86 is kept open, the passage of blades 71, 72 and 73 over contact elements 69, 70 is without effect. Thus, depending on the time interval during which switch 86 is kept open, which may be set on device 87, the stepwise rotation of rotor 1 through 120° angles may be continued over several complete rotations. Nevertheless, the rotor will stop always in the desired precise angular position wherein the tubes 13 will be occluded by two rollers, at the time that one of the blades 71, 72 or 73 first passes over contact elements 69, 70 after switch 88 has been closed.

During it continued rotation, cam 42 opens switch 53 controlled by cam follower 46, thus interrupting the current supply line A to motor M41 so that the latter stops.

Thus, a brief depression of switch button 49 has caused the rotor 1 to rotate clockwise through 240°, as well as operating air pump P40.

To continue the operating cycle, the operator must close switch 54 which is connected in parallel with selector switch 53 so as to reconnect selector switch motor M41 to current supply circuit line A. Thus, the cam 42 will open switch 55 controlled by cam follower 47, which not only interrupts circuit line a4 supplying current to relay R38 but also circuit line a3 leading to switch 60/61 and thence to circuit line d so that relay R39 is also disconnected.

The de-energization of relay R39 has the effect of opening switch 62/63, which stops operation of air pump P40, as well as opening switch 64/65 while closing switch 64/66, so that the motor M24 is now supplied with current through conductor F rather than E, which reverses the direction of rotation of the rotor into a counterclockwise direction until blade 72 closes the contact, and thus the relay R38 is again supplied with current through circuit line a4 while power is shut off from motor M24 after a 120° rotation of rotor 1. In the course of this reverse rotation, the lamp 68 signals.

As soon as cam 42 again operates cam follower 43, it reopens switch 50, stopping selector motor M41 in its initial position.

In summary, once the principal switch 48 is operated to close contact Z and open contact Y, a pressure on button 49 causes the rotor to rotate through two successive 120° angle steps and simultaneously operates air pump P40. Then, closure of switch 54 causes the rotor 1 of pump P1 to rotate counter-clockwise by 120° and simultaneously stops the air pump.

If switch 54 is kept closed, these two operative stages of pump P1, i.e. two steps forward and one step backward, continue automatically.

In view of the regular distribution of the contact blades 71 to 73 on insulating collar 28 rotating in unison with rotor 1, the rotor will stop between steps always in the perfect angular position determined by the location of the blades.

As shown in FIG. 6, the rotor will be stopped always in such a position that two pressure rollers 4 engage the tubes 13 at the beginning and at the end of each liquid distributing period. This blade arrangement is particularly advantageous because the return of the liquid produced at the moment when the roller no longer crushes the tubes and they assume their open form, takes place at the beginning of the feeding cycles.

However, as shown in FIG. 7, it is also possible so to arrange the insulating collar 28 with its contact blades (see broken lines in FIG. 5), that only a single roller will be in crushing engagement with the tubes 13 when the rotor is stopped.

In both modifications the rotor 1 is always stopped in such successive angular positions that the tubes are effectively occluded at the same spot by the rollers. This assures the distribution of precise doses of liquid by the peristaltic pump, which remain rigorously constant.

As shown in FIG. 8, the installation is placed in operative condition by actuating principal switch 48 so that contact Z is open and contact Y is closed. Closure of contact Y assures the direct energization of relay R39, which closes switch 64/65 and thus entrains motor M24 of pump P1 in a clockwise direction. With contact Z open, the relay R38 is not energized so that switch 56/57 of supply circuit line C remains closed. Therefore, the pump rotor is rotated clockwise as long as switch 48 remains in this position.

The pump rotor is permitted to continue to rotate clockwise until diluent pumped thereby from reservoir 84 begins to run through nozzles 77. At this point, principal switch 48 is thrown to open contact Y and close contact Z. The pump rotor is thus stopped at an angular position determined by one of the blades 71, 72 or 73 establishing contact between contact elements 69, 70. This energizes relay R38 and interrupts the power supply to motor M24 because of the opening of switch 57/56. Therefore, the tubes 13 are completely filled with liquid diluent received from reservoir 84.

This preparatory stage of operation takes place while the selector switch SL is in an angular position wherein cam follower 46 is operated by cam 42. The selector is automatically stopped in this position when switch 54 is open. The nozzles 77 are now immersed in the liquid to be diluted which is contained in the first containers 80 carried by mobile carriage 75, the immersion of the nozzles being effected manually by lowering support 76. This position is indicated at 1 in FIG. 9, the nozzle full of diluent liquid D being plunged into the liquid L to be diluted which is contained in test tube 80.

At this point, switch 54 positioned on support 76 is operated, which may be done easily by a movement of the thumb while the operator's hand grips handle 96, which permits selector cam 42 to resume its forward rotation and to actuate cam follower 47 controlling switch 55. Opening switch 55 causes the pump rotor to rotate one step backwards so that samples E1 of a predetermined and controlled volume of the liquid to be diluted are removed from containers 80 through nozzles 77, as shown at II in FIG. 9. This operating stage is signaled by illumination of lamp 68. Rotation of cam 42 stops as soon as it reaches operative contact with cam follower 42, due to the opening of switch 50.

Figure 9:
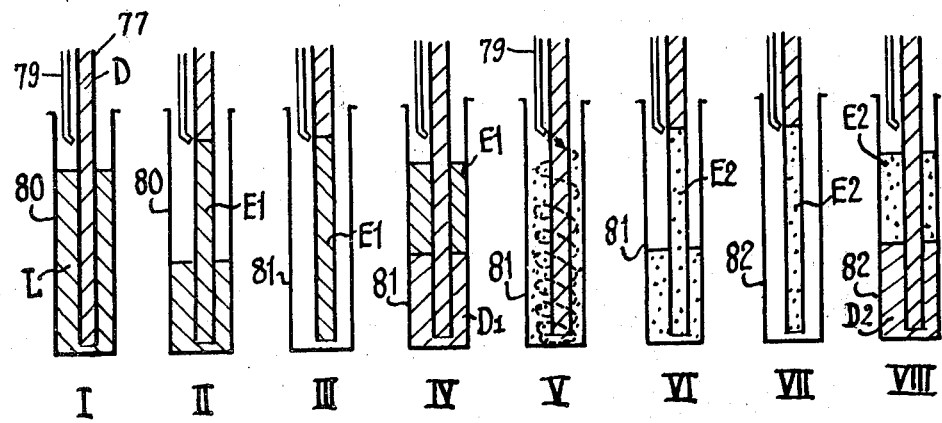
FIG. 9 schematically illustrates the geometric liquid distribution by the method of the invention.

The carriage 75 is now displaced to the left after the nozzles have been lifted out of test tubes 80, and the nozzles are placed into the succeeding series of test tubes 81, which are empty, as can be seen at stage III in FIG. 9.

At this point, button 49, which is also located on support 76, is briefly depressed to initiate the forward rotation cycle of rotor 1 of pump P1. Lamp 67 again lights up and rotor 1, turning two 120° steps forward, first discharges the samples E1 into test tube receptacles 81 and then discharges an equal amount D1 of diluent thereinto, as shown at IV in FIG. 9. The two liquid portions are intimately mixed in test tubes 81 by the simultaneous discharge of air biased onto the surface of the fluid through nozzles 79, see stage V in FIG. 9.

Switch 54 being closed, the following sample E2 is now removed from test tubes 81 by the opening of switch 55, which stops air pump P40 and causes a reversal in the rotary movement of the pump rotor, and the selector SL is stopped when cam 42 operates cam follower 43 opening switch 50 (stage VI of FIG. 9). As previously described, the nozzles 77 are now displaced into the next series of empty test tubes 82, as shown at VII in FIG. 9, switch button 49 is again depressed momentarily and a new complete operating cycle begins with the deposit of sample E2 therein and, subsequently, and equal amount of diluent D2 (stage VIII in FIG. 9).

Thus, dilutions of the liquid to be diluted are obtained in a geometric series of the factor 2, which factor may be modified at will by operation of the adjustable timing device 87.

The above-described apparatus has the following advantages:

1. A single peristaltic pump assures not only the evacuation of a liquid sample from a test tube but also its redistribution in a mixture with an additional dose of an equal amount of diluent.

2. The two liquid portions are dosed in the same tube so that a very precise dilution in geometric proportion is easily obtained. Changes in the cross section of the tubes or in other parameters have no influence on the accuracy of the dilution rate of the liquids. The reproducibility of the results is almost absolute.

3. Since the tubes are rinsed by the dose of diluent which follows the distribution of a sample, all contamination of successive samples is avoided. Thus, the pump is ready immediately for the removal of the following sample.

4. Since the control circuit stops the rotor in exact predetermined angular positions, each tube is always compressed at the same places by the same number of pressure rollers after each operational step so that the doses distributed during each rotational step are rigorously identical.

As already explained, the pump may also be controlled by timing device 87, during its forward or backward rotation, to increase the number of operating steps so as to modify the rate of progression of the dilution or the working volume. Also, the pump may comprise more than three pressure rollers.

An apparatus of this type is particularly useful to a. meter accurately reproducible doses of liquids, for instance to remove a predetermined quantity from a first receptacle and to distribute it in another receptacle;

b. remove samples of a constant quantity from a first liquid product, and add to these samples a diluent of a predetermined quantity; and c. prepare dilutions in an accurate geometric progression.

What is claimed is:

1. A method of geometrically diluting a liquid in a series of successive containers in twofold increasing dilutions with a diluent liquid, comprising the combination of steps of peristaltically pumping accurately metered doses of the diluent liquid through a flexible tube from an upstream end of the tube in communication with a supply of the diluent liquid to a downstream end of the tube in successive communication with each of the successive containers, the downstream tube end holding selected number of the metered doses of the diluent liquid, immersing the downstream tube end in a first one of the successive containers containing the liquid to be diluted, peristaltically pumping an accurately metered dose of the liquid from the first container, withdrawing the downstream tube end holding the accurately metered dose of the liquid to be diluted and the selected number of the metered doses of the diluent liquid from the first container, immersing the downstream tube end in a second one of the successive containers, peristaltically pumping the metered dose of the liquid to be diluted and an equal dose of the succeeding diluent liquid into the second container, mixing the liquid to be diluted and the diluent liquid in the second container to obtain an accurately metered dose of a first diluted liquid and continuing the cycle of withdrawing and immersing the downstream tube end, peristaltic pumping and mixing in successive ones of the containers.

2. The method of claim 1, wherein the liquids are mixed by a rotary movement induced therein by an air jet biased onto, and repelled by, the surface of the liquids.

3. In a peristaltic dilutor system, the combination of a flexible tube having an upstream end and a downstream end; a supply of diluent liuqid in communication with the upstream end of the flexible tube for filling the tube with diluent liquid; a supply of liquid to be diluted in communication with the downstream tube end; a peristaltic pump arranged between the upstream and downstream ends of the flexible tube, the pump having a rotor with a rotary shaft and a plurality of rollers distributed concentrically about the rotary shaft and angularly spaced equidistantly thereabout, a concavely arcuate pumping shoe dimensioned and mounted for simultaneous cooperation with two of the peristaltic pump rollers, the flexible tube being laced between the shoe and the rotor rollers, and the spacing between the shoe and the rotor rollers being such that the tube is compressed by the rollers pressing it against the shoe when the rotor rotates the rollers into engagement with the tube whereby the tube is occluded locally at equidistantly spaced points along the length of the tube during rotation of the rotor, control means for intermittently entraining the rotor for rotation through predetermined angular portions of a full rotation corresponding to the angular spacing between two successive rollers in alternate directions whereby stopping of the rollers in the same angular position is invariably insured, rotation in one of said directions for each of said angular portions propelling a first dose of the liquid at the downstream end of the flexible tube inwardly, and rotation in the opposite direction for a plurality of angular portions propelling outwardly at said downstream tube end the first dose of liquid and dose of the diluent liquid propelled by the pump from the upstream end of the tube, means for supporting a succession of the supplies of liquid to be diluted for displacement in respect of the downstream tube end, means for successively immersing and withdrawing the downstream tube end in and from each of the liquid supplies of the succession, the first dose of the liquid being inwardly propelled from each of the liquid supplies by the rotor rotation in the one direction when the downstream tube end is immersed therein and this liquid dose being retained in the downstream tube end after the downstream tube end has been withdrawn, the rotor being rotated in the opposite direction after the downstream tube end has been immersed in a successive one of the liquid supplies to propel the first dose of the liquid and the dose of the diluent liquid outwardly into the successive liquid supply, and repeating the cycle of operation in further liquid supplies so as to obtain series of stepwise increasing dilutions of the liquids, automatically controlled air jet means for mixing the doses of liquid in the successive liquid supply, the air jet means including air pump means operable to discharge an air stream through a discharge opening when the peristaltic dilutor system delivers fluid to the liquid supply, and to stop when fluid is withdrawn from said liquid supply, air conduit means, and air jet directing means connected by the air conduit means to the discharge opening of the air pump means, and operable to bias the air stream onto the surface of any fluid present in the liquid supply from a point eccentrically located above the surface of the liquid, in such a way that the air, when repelled by the surface of the liquid, induces a rotary movement in the liquid.

* * * * *